United States Patent
Vladyka, Jr. et al.

(10) Patent No.: US 6,497,905 B1
(45) Date of Patent: Dec. 24, 2002

(54) AQUEOUS SOLUBILITY PHARMACEUTICAL FORMULATIONS

(75) Inventors: Ronald S. Vladyka, Jr., Somerset, NJ (US); David F. Erkoboni, Pennington, NJ (US); Pamela R. Stergios, Plainsboro, NJ (US)

(73) Assignee: R.P. Scherer Technologies, Inc., Paradise Valley, NV (US)

( * ) Notice: Subject to any disclaimer, the term of this patent is extended or adjusted under 35 U.S.C. 154(b) by 0 days.

(21) Appl. No.: 09/528,624

(22) Filed: Mar. 20, 2000

Related U.S. Application Data

(60) Provisional application No. 60/125,914, filed on Mar. 24, 1999, and provisional application No. 60/149,680, filed on Aug. 19, 1999.

(51) Int. Cl.[7] .......................... A61K 9/16; A61K 47/32; A61K 47/38; A61K 47/44; A61K 47/26; A61K 31/4196; A61K 31/496; A61K 31/357

(52) U.S. Cl. ...................... 424/502; 424/501; 424/499; 514/383; 514/384; 514/471; 514/254.07

(58) Field of Search ................................. 424/502, 489, 424/480, 476, 470, 465, 501, 499; 514/383, 384, 471, 254.07

(56) References Cited

U.S. PATENT DOCUMENTS

| | | | |
|---|---|---|---|
| 4,727,064 A | 2/1988 | Pitha | 514/58 |
| 4,764,604 A | 8/1988 | Muller | 536/103 |
| 5,118,799 A | 6/1992 | Rossignol | 536/7.2 |
| 5,208,015 A | 5/1993 | Shah et al. | 424/78.05 |
| 5,225,206 A * | 7/1993 | Fushimi et al. | 424/490 |
| 5,565,478 A | 10/1996 | Kohn et al. | 514/359 |
| 5,633,015 A | 5/1997 | Gilis et al. | 424/490 |
| 5,646,151 A | 7/1997 | Kruse et al. | 514/255 |
| 5,707,975 A | 1/1998 | Francois et al. | 514/58 |
| 5,776,495 A | 7/1998 | Duclos et al. | 424/455 |
| 5,830,501 A | 11/1998 | Dong et al. | 424/473 |
| 5,972,381 A * | 10/1999 | Sangekar et al. | 424/451 |
| 5,976,555 A | 11/1999 | Liu et al. | 424/401 |
| 5,998,413 A | 12/1999 | Heeres et al. | 514/252 |
| 6,096,338 A * | 8/2000 | Lacy et al. | 424/455 |

FOREIGN PATENT DOCUMENTS

| | | |
|---|---|---|
| EP | 0 197 571 B1 | 10/1986 |
| EP | 0 462 066 A1 | 12/1991 |
| EP | 0852140 A1 | 8/1996 |
| WO | WO 93/15719 | 8/1993 |
| WO | WO 97/18839 | 5/1997 |
| WO | WO 97/44014 | 11/1997 |
| WO | WO 98/42318 | 10/1998 |
| WO | WO 98/43513 A1 | 10/1998 |
| WO | WO 98/55148 | 12/1998 |
| WO | WO 98/57967 | 12/1998 |

* cited by examiner

Primary Examiner—Edward J. Webman
Assistant Examiner—Helen Nguyen
(74) Attorney, Agent, or Firm—Donald O. Nickey; Patrick J. Farley

(57) ABSTRACT

A formulation of a sparingly water-soluble, crystalline pharmaceutically active agent wherein the active agent is converted to and stabilized in its amorphous form as a solid solution of a normally hydrophobic vehicle is described. The amorphous state is stabilized by the composition of the formulation, providing long shelf life of the improved composition. This stabilized formulation also provides increased solubility and bioavailability of the active agent. Solutions of the active agent are stabilized by the composition, preventing recrystallization and precipitation of the less soluble, crystalline form of the active agent from aqueous solutions thereof.

21 Claims, No Drawings

AQUEOUS SOLUBILITY PHARMACEUTICAL FORMULATIONS

This application claims benefit of Prov. No. 60/125,914 filed Mar. 24, 1999 which claims benefit of Prov. No. 60/149,680 filed Aug. 19, 1999.

This invention relates to methods and formulations for improving the aqueous solubility of crystalline pharmaceutical compounds having low water solubility by converting them to an amorphous state that is stabilized in a granular pharmaceutical formulation. In particular, it relates to improving the aqueous solubility and bioavailability of azole antifungal medicaments by converting them to the amorphous state, stabilizing this state, and granulating them to form a stabilized granulation thereof. It also relates to pharmaceutical formulations prepared by such methods, to solid dosage forms prepared therefrom, and stabilized aqueous solutions thereof.

BACKGROUND OF THE INVENTION

Many crystalline, pharmaceutical compounds have very slight solubility in aqueous fluids such as those found in the human body. It is well known that changing a crystalline compound into its amorphous state will substantially increase the aqueous solubility of the compound, thereby increasing its bioavailability.

Methods which have been used heretofore to improve aqueous solubility of sparingly soluble active ingredients include inclusion complexation of the active ingredient with amorphous, chemically modified cyclodextrins. Although the active ingredient is not converted from the crystalline state to the amorphous state, the active ingredient/cyclodextrin complex improves solubility of the sparingly soluble ingredients.

In some cases it is possible to melt the crystalline active agent, holding it in the molten state for a finite time and then allow it to cool to an amorphous solid. This method is limited to particular active ingredients which can produce stable amorphous solids and which are not degraded by the heating step.

European patent publication 0852140 A1 discloses a method of converting a sparingly soluble medical substance to a more water-soluble amorphous state, in which a mixture of a sparingly water-soluble medical substance, an amorphous state inducing agent and an amorphous state-stabilizing agent, such as hydroxypropylmethylcellulose, is reported to be heated to a temperature at which the medical substance becomes amorphous.

A methylene chloride solution of an antifungal agent which is dissolution-induced dried by any of several methods, e.g., spray dried, initially at a slow rate and then at a higher rate, produces an amorphous powder of the active ingredient. This powder may then be compacted and dry granulated with excipients to be used in tablets or hard gelatin capsules.

In another procedure to produce amorphous antifungal agents, the agent and hydroxypropylmethylcellulose are dissolved in a methylene chloride/alkanol solution. This solution is then sprayed onto spheres such as sugar spheres in a fluidized bed. A seal coating is then applied to the coated spheres which may then be used to fill hard gelatin capsules.

In another procedure to form an amorphous solid dispersion, a sparingly soluble active agent has been combined with polyvinylpyrrolidone when both components are molten and then allowed to cool. This method reportedly produces a more rapid dissolution of the active agent in water.

A further method for stabilizing itraconazole in its amorphous state is through melt-extruding a mixture of itraconazole and a) water soluble polymer, as set forth in International Application PCT\EP97\02507.

The above methods appear to have varying degrees of success in improving the solubility of a sparingly soluble active agent. However, significant improvement in bioavailability also requires that the resulting solution of the active ingredient be stable. Without this stabilization, crystallization and precipitation of the dissolved active agent may occur, thereby reducing the bioavailability of the active agent that has not yet been absorbed into the patient's bloodstream.

SUMMARY OF THE INVENTION

In accordance with the present invention, improved solubility and bioavailability of a sparingly water-soluble, crystalline pharmaceutically active agent, such as itraconazole, involves melting a normally solid hydrophobic vehicle, such as glyceryl monostearate, dissolving therein a sparingly water-soluble, normally crystalline (that is a compound which is, prior to processing hereunder into its amorphous form, crystalline and sparingly water-soluble at ambient temperature pressure) pharmaceutically active agent at a temperature above the normal melting temperature of the vehicle but below the normal melting or degradation temperature of active agent, then granulating the molten product with a disintegrant and optional additives. In a first embodiment, a stabilizer is added to the molten solution prior to granulation. In a second embodiment the molten solution is granulated with a mixture of a-stabilizer and a disintegrant. In the first embodiment the granulation is preferably conducted in a cooled granulation bed to rapidly cool the stabilized product. In the second embodiment the granulation is conducted at elevated temperature and the resulting granulate is rapidly cooled following a brief granulation period. The resulting granular particles may then be milled to an appropriate particle size, and filled into capsules, or blended with other excipients and processed into solid dosage forms.

The resulting product of this invention thus comprises a granular formulation in which the granular particles comprise a solid solution of an amorphous pharmaceutically active agent which is normally crystalline and sparingly water-soluble at ambient temperature and pressure, dissolved in a molten solution of a pharmaceutically acceptable normally solid hydrophobic vehicle in which the active agent is soluble at elevated temperature; a stabilizing agent to stabilize the active agent in its amorphous state; a disintegrant; and optionally a binder, wherein the dissolved active agent is substantially stabilized in an amorphous state as a solid solution in said granular particles.

Thus a complete, ready-to-use granular formulation is provided in which the amorphous state of the active agent is stabilized for an extended period of time as a solid solution of the amorphous active in the matrix of the hydrophobic vehicle, thereby increasing the solubility and bioavailability of the pharmaceutically active agent when ingested and passing into aqueous media such as that found in the stomach and providing an extended shelf life for the granulation and products made therefrom.

DETAILED DESCRIPTION OF THE INVENTION

The novel formulations of this invention that are useful to solubilize sparingly water-soluble normally crystalline pharmaceutically active agents in aqueous media include a normally solid hydrophobic vehicle, one or more stabilizers, binders, and disintegrants. Basic to the solubilization of a normally crystalline active agent is the necessity of converting it to its amorphous state as a solid solution, and then stabilizing the amorphous state, thus preventing reversion to the crystalline state. The formulations of this invention accomplish this stabilization of the amorphous state of an active agent and maintain it for extended periods of time, providing an extended shelf life for the active agent during which it has improved solubility and bioavailability. A further, unexpected benefit of these formulations is the stabilization of solutions that are prepared from the granular formulations of the solubilized active agent. Such solutions are or may be essentially supersaturated with respect to the intrinsic solubility of the active ingredient, but stabilization in accordance with the present invention substantially prevents recrystallization from occurring.

The novel granular formulations of this invention thus comprise (a) a solid solution of a pharmaceutically active agent which is sparingly water-soluble its normal crystalline state; (b) a normally solid hydrophobic vehicle for said pharmaceutically active agent such that said vehicle is capable of dissolving said pharmaceutically active agent at a temperature above the melting point of said vehicle but below the normal melting point of said pharmaceutically active agent; (c) a stabilizer comprising a member selected from the group consisting of a polyethylene glycol, sugars, sorbitol, mannitol, polyvinylpyrrolidone, and cellulose ethers such as methylcellulose, hydroxypropylmethylcellulose, and hydroxypropylcellulose and the like; (d) a disintegrant comprising a member selected from the group consisting of croscarmellose sodium, sodium starch glycolate, crospovidone, and a cross-linked polyacrylate, wherein the normally sparingly water-soluble active agent is dissolved and stabilized in an amorphous state as a solid solution in said vehicle. Depending on the active ingredient and the amounts of the various components, the granulation of this invention may also include a binder, filler or other conventional excipients.

More particularly, the granular formulations of this invention are those in which the granular particles comprise (a) a solid solution of the pharmaceutically active agent in a substantially amorphous state in a solid matrix of the vehicle, more specifically, a solid solution of an amorphous, pharmaceutically active agent and the pharmaceutically acceptable hydrophobic vehicle, wherein the pharmaceutically active agent is normally crystalline and sparingly water soluble at ambient pressure and temperature and wherein said pharmaceutically active agent is dissolved and stabilized in a substantially amorphous state in a molten solution of said vehicle; (b) a stabilizer, and (c) a disintegrant. As used in this application, the phrase 'solid solution' means the active agent has been subjected to a treatment in which the active agent is dissolved in a molten solution of the hydrophobic vehicle and, through additional processing, is solidified.

Suitable vehicles for the pharmaceutically active agent are pharmaceutically acceptable hydrophobic vehicles which are normally solid at ambient temperature, but which melt without degradation at temperatures below the normal melting or degradation temperature of the pharmaceutically active agent. In addition the characteristics of the vehicle must be such that it is capable of dissolving the active agent at a temperature above its own melting point but below the melting point of the active agent. More specifically the vehicles of this invention should have a melting point above about 60° C. and should be stable to a temperature up to the temperature at which the active ingredient becomes soluble in the vehicle. Depending on the active ingredient the vehicle should be stable at least to 140° C., and more preferably to a temperature up 250° C. or even slightly higher. Further it must not be volatile or evaporate or degrade when heated to such temperatures. The precise choice of vehicle will depend in part on the active agent and in particular on its solubility profile. For solubilization of azole fungicides such as itraconazole a preferred vehice is glyceryl monostearate, however various other long chain monoglycerides, diglycerides, and triglycerides, and waxes, including beeswax and microcrystalline wax, and mixtures thereof may also be suitable vehicles for the purpose of this invention. The total amount of vehicle that may be used effectively ranges from about 3% to about 55% by dry weight of the granular formulation. In a preferred embodiment in which glyceryl monostearate is the vehicle, its concentration should be from about 5% to about 50% by dry weight of the formulation, more preferably about 5% to about 35%.

In addition to acting as a vehicle for dissolution of the active agent, it is probable that the vehicles used in this invention may also serve a second beneficial function in the granular formulation, namely to stabilize or assist in the stabilization of the active ingredient in its amorphous state and thus to prevent it from reverting to its normal crystalline state during and after granulation.

Stabilizers conventionally employed to stabilize the active agent in its amorphous state and prevent reversion to its normal crystalline state are also employed in the invention. These materials also serve as pore formers and are necessary in these granular formulations to promote the entrance of water into the body of the granules containing the stabilized amorphous active agent. By providing a path for the water to enter the granules, the dissolution of the amorphous active agent is promoted. Suitable stabilizers include polyethylene glycols, other polyols, sugars, sorbitol, mannitol, polyvinylpyrrolidone, and cellulose ethers such as, for example, methylcellulose, hydroxypropylmethylcellulose, hydroxypropylcellulose, and mixtures thereof. A preferred stabilizer which also serves as a pore former for granules of the active agent is hydroxypropylmethylcellulose. The stabilizer is suitably present in the granular formulations of this invention in the range of about 1% to about 60% by weight of the dry granulation, preferably about 1% to about 50%.

Glycerin may also be employed in the present formulation and when present is believed to assist as a pore former and in some instances as an aid to dissolution of the active ingredient, but is not believed to exhibit any substantial benefit in stabilizing the active agent in its amorphous form. When used it may be suitably employed at about 15% to about 30% by weight of the dry granular particles of this invention.

Appropriate disintegrants to be used in these formulations are referred to as super disintegrants. Included in this category are croscarmellose sodium (cross-linked carboxymethylcellulose), sodium starch glycolate, crospovidone (cross-linked polyvinylpyrrolidone), and cross-linked polyacrylates. A preferred disintegrant is croscarmellose sodium which may be present in the formulation from about 1% to about 25% by dry weight of the formulation, preferably from about 3% to about 25%.

Binders may be selected from microcrystalline cellulose, cellulose floc, starch, sugars, e.g., lactose or sucrose, calcium phosphate, calcium carbonate, and kaolin. A preferred binder is microcrystalline cellulose, such as Avicel® PH-101. The range in which the binder is present is from about 5% to about 35% by dry weight of the formulation, preferably from about 5% to about 20%.

Suitable active agents are those which are normally crystalline at ambient temperature and in that state are no more than sparingly soluble in aqueous media, have a melting point between 50° C. and 200° C. and possibly as high as about 300° C., may be converted to their amorphous state by heating, and tend to revert to the normal insoluble crystalline state when cooled and re-solidified. In general the term sparingly soluble as applied to active agents for use in the present invention relates to active agents which in their normal crystalline form have very limited aqueous solubility at ambient temperature, which include substances whose solubilities range from slightly soluble (=1:100 to 1:1000) to insoluble (more than 1:10,000). By stabilizing these active agents in their amorphous state in a solution of a hydrophobic vehicle either prior to or during granulation, a stabilized granulation is provided in which the active agent is stabilized in that amorphous state for extended periods of time, thereby providing desirable shelf life and increasing their solubility and bioavailability. Actives having a melting point below about 50° C. would not be expected to be stabilized, at least for the period required for a satisfactory shelf life. Further, the active agent must be stable at or above the temperature at which it dissolves in the molten stabilizer. If decomposition occurs, it not only reduces the amount of active present in the formulation, but it also presents the possibility of decomposition products being introduced into the formulation. From a manufacturing perspective, temperatures in excess of about 250° C. become increasingly expensive, making other methods of solubilization and stabilization more economical.

For example, this method of increasing active agent solubility is applicable to the class of antifungal agents referred to as azoles, including ketoconazole, itraconazole, saperconazole, fluconazole, miconazole, and the like. All members of this class of active agents have very low solubility in aqueous media and will benefit from the method of conversion to the amorphous state and stabilization of that state that is described herein. More specifically, it has been applied to itraconazole very effectively. The concentration of itraconazole can be varied to provide a particular dosage in a convenient form. Typically this concentration may range from about 5% to about 60% by weight of the granular formulation. In a preferred formulation this concentration range is about 20% to about 35%.

Formulations of this invention containing itraconazole have demonstrated a high rate of dissolution. Within 30 minutes 36–86% of the itraconazole dissolved in simulated gastric juice. By comparison, after 30 minutes under the same conditions, only 1% of crystalline itraconazole had dissolved. After 60 minutes, these values increased to 45–95% for the amorphous, stabilized itraconazole compared with only 2% for the crystalline material. Not only was the solubility of the itraconazole dramatically increased, but also the resulting solution was stabilized so that itraconazole did not recrystallize and precipitate from the solution.

Mention has been made of the stabilizing effect of the novel formulations described herein on the aqueous solutions produced by dissolution of the formulations. Although it may be possible to identify components of the formulation which have a greater probability of effecting the stabilization of these solutions, it is believed that the entire formulation and the interaction of its components is required for this stabilization to occur to the extent that has been observed. Accordingly, the granular particle of this invention may comprise from 20% to about 35% of pharmaceutically active agent, preferably itraconazole, about 5% to about 35% of the hydrophobic vehicle, preferably glyceryl monostearate, about 3% to about 25% of the disintegrant, preferably croscarmellose, and about 1% to about 50% of the stabilizer, preferably hydroxypropylmethyl cellulose, all by dry weight of the granular particle.

In one particularly preferred embodiment the granular particle described generally above contains from about 15% to about 25% hydroxypropylmethylcellulose, most preferably about 20%, and about 5% to about 15% of microcrystalline cellulose as a binder, most preferably about 10%, as illustrated in example 5.

In another particularly preferred embodiment the granular particle contains from about 30 to 35% active agent, preferably itraconazole, about 5% to 15% glyceryl monostearate, about 10% to 15% croscarmellose sodium, and 45% to about 55% hydroxypropylmethylcellulose, all by weight of the granular particle, as illustrated in examples 6 and 7.

In the first method aspect of this invention, the preparation of the stabilized granular formulations of this invention involves the following steps:

(a) heating the hydrophobic vehicle to a temperature at which the vehicle melts and to or slightly above a temperature at which the active agent dissolves in the molten vehicle;

(b) dissolving the pharmaceutically active agent in the molten vehicle to form a molten solution of the pharmaceutically active agent in said vehicle;

(c) adding a stabilizing amount of the stabilizer to the molten solution;

(d) granulating the molten mixture from (c) with a disintegrant and optionally a binder at a temperature below about 30° C., preferably below about 5° C.; thereby forming granular particles comprising a solid solution of the pharmaceutically active agent stabilized in its more soluble amorphous form in the hydrophobic vehicle.

In the second method aspect of this invention, the preparation of these formulations is modified to comprise the following steps:

(a) heating the hydrophobic vehicle to a temperature at which the vehicle melts and to or slightly above a temperature at which the active agent dissolves in the molten vehicle;

(b) dissolving the pharmaceutically active agent in the molten vehicle to form a molten solution of the pharmaceutically active agent in the vehicle;

(c) granulating the molten solution with a mixture of the stabilizer, the disintegrant and optionally a binder at or above the temperature at which the active agent dissolves in the stabilizer, to form a granulate; and (d) rapidly cooling the resulting granulation.

The temperature at which the active agent dissolves may, in some cases, be lower than the melting temperature of the active agent. It must, however, be high enough to cause the solution to form rapidly and completely. In the first embodiment the stabilizer is added directly to the molten solution of vehicle and active agent and the resulting molten product is then granulated with a cold mixture of a binder and disintegrant and optionally other excipients, under conditions which will cause rapid cooling of the molten material as granulation proceeds, thereby minimizing the amount of active ingredient which can revert to its normal insoluble crystalline state. For example the granulator may suitably be operated at ambient temperature or at any temperature below about 30° C., but is preferably operated at a temperature below about 5° C. In the second mode the stabilizer, rather than being added directly to the molten solution, is instead mixed with the disintegrant and optionally one or more binders or other excipients, and the molten solution is then granulated with that mixture. For this embodiment the granulator is preferably operated at or about the temperature at which the active agent dissolves in the vehicle, thereby stabilizing the active agent in the amorphous state before it has an opportunity to revert to its normal crystalline state, then rapidly cooling the granulate, suitably by discharging the hot granulate through liquid nitrogen.

It will be appreciated by those skilled in the art that depending on the specific properties of the active agent and the vehicle, that even under ideal conditions there may be small amounts of active agent which will not dissolve in the vehicle and therefore do not convert to the amorphous state, but such amounts are believed to be insignificant relative to the large proportion of material that goes into the solid solution which forms the basis for this invention. A small portion thereof may revert to the normal water-insoluble crystalline state of the active ingredient, thereby reducing the amount of active available for treatment of disease. While these amounts are difficult to quantify using known analytical techniques, it is believed and it is desirable that at least 85% of the active ingredient, advantageously 90%, or preferably at least 95% to 99% or even 100% of the active ingredient used be present in the granules as an amorphous solid in the resulting solid solution.

It will also be apparent to those skilled in the art that if the dissolution temperature is too high and/or elevated temperature is maintained for too long a period of time during processing, that the active agent may partially degrade forming degradation products in the granular particles.

The selection of which the two modes of operation to choose and/or the precise conditions under which to operate either of them may depend on several factors. Both modes have been shown to be viable and useful options which achieve the foregoing objectives with itraconazole and glyceryl monostearate. In general however, it is preferred to carry out the dissolution step at or about the lowest temperature at which the active agent dissolves in the vehicle, and to avoid heating the vehicle and/or solution of vehicle and active agent to a temperature above that at which the active ingredient begins to undergo significant degradation. With itraconazole, dissolution and processing of the stabilized solution is preferably carried out at a temperature below the melting point of itraconazole.

Although it may be preferable to use a high shear granulator to produce the final formulation, it is possible that granulators such as extrusion granulators, fluid bed granulators, spray congealers, and spray dryers may be used equally well, provided the necessary cooling is available to firmly establish the amorphous character of the active ingredient.

If the particles of the final granulation are undesirably large, it is suitable to grind them and screen them to a more acceptable, more uniform size. In this case, the grinding may be done with effective cooling, e.g., that amount of cooling which is necessary to prevent reversion of the active ingredient to the crystalline state and at the same time provide sufficient brittleness for effective grinding. Using liquid nitrogen or some other method of cooling is generally acceptable.

Granules that are produced by this invention may be placed directly into hard gelatin capsules to create the final dosage form. A lubricant or a flow aid can be added to these granules to improve flowability into the capsules, if necessary. Additionally, materials granulated by the method of the second aspect of this invention may benefit from the granulate being dry blended with a binder, and, optionally, an additional disintegrant. If, on the other hand, it is desired to compress the granules into tablets using a tableting machine, the addition of a lubricant may be necessary to prevent the processing problems associated with this operation. Both methods of delivery are contemplated as being part of this invention.

The following examples are provided to demonstrate the methods of making and using this invention, but they are only to be construed as being exemplary of the invention, and not as limiting it. Those skilled in the art will understand that obvious variations can be used and are included within this invention. In these examples, unless otherwise specifically stated, all percentages are in weight % of the granular formulation, and all temperatures are in degrees centigrade.

Further, the dissolution rate of each formulation was determined using a USP Apparatus 2 (paddle), operated at 100 rpm and containing 900 mL of simulated gastric fluid without pepsin. This fluid was heated to 37° C., and a sample of the granulation containing 100 mg of the active agent was employed. Measurements were taken after 30 minutes and 60 minutes. To determine the total amount of active that was soluble, the stirring was increased to 200 rpm after the 60 minute reading, and the final reading was taken two hours later. This final determination provides a crude measure of the effectiveness of the stabilization of the amorphous state by the formulation; 100% dissolution equates to complete conversion to the amorphous state and 100% stabilization of that state.

EXAMPLE 1

A beaker containing 11.88 grams of glycerin was heated to between 90° C. and 100° C. To the hot glycerin was added 11.88 grams of glyceryl monostearate (Eastman Chemical Company). This mixture was stirred until the glyceryl monostearate was fully dispersed, and then the temperature was raised to between 130° C. and 150° C. at which time 12.50 grams of itraconazole was added to the molten mixture. Stirring was continued until the itraconazole was fully dissolved, yielding a clear solution. To this solution was added 1.25 grams of hydroxypropylmethylcellulose E4M (Dow Chemical Company) with continued stirring. Simultaneously, a mixture of 12.50 grams of microcrystalline cellulose (Avicel® PH-101, FMC Corporation) and 12.50 grams of croscarmellose sodium (Ac-Di-Sol®, FMC Corporation) was placed in a granulator bowl cooled in a water bath at 25° C. The molten mixture was then added to the solids in the granulator bowl with mixing until the temperature of the entire mixture reached 25–30° C. Dissolution testing showed that 43% of the itraconazole dissolved in 30 minutes, and after 60 minutes the dissolved itraconazole increased to 51%. Under the same conditions, the values for the dissolution of crystalline itraconazole were determined to be 1% and 2% at 30 and 60 minutes, respectively.

EXAMPLE 2

By the method of Example 1, 7.5 grams of glycerin, 7.5 grams of glyceryl monostearate, and 15.5 grams of itraconazole were melted together. The itraconazole went into solution at 144° C. To this molten mixture was added 1.5 grams of methylcellulose A15C. The viscosity of the resulting dispersion appeared to be lower than the viscosity of the comparable dispersion in Example 1. This dispersion was then granulated with a mixture of 15.5 grams of Avicel® PH-101 and 2.5 grams of croscarmellose sodium. Dissolution testing determined that 43% of the itraconazole had dissolved in 30 minutes. After 60 minutes this value had increased to 54%.

EXAMPLE 3

By the method of Example 1, 11.88 grams of glycerin, 5.94 grams of glyceryl monostearate, and 12.5 grams of itraconazole were melted together. To this molten mixture was added 1.25 grams of hydroxypropylmethylcellulose E4M. The molten phase mixed well and was very fluid. This dispersion was then granulated with a mixture of 7.37 grams of Avicel® PH-101 and 7.37 grams of croscarmellose sodium. This granulation was comprised of relatively small granules and appeared to be particularly uniform in appearance. Dissolution testing determined that 51% of the itraconazole had dissolved in 30 minutes. After 60 minutes this value had increased to 61%.

EXAMPLE 4

By the method of Example 1, 11.88 grams of glycerin, 2.97 grams of glyceryl monostearate, and 12.5 grams of itraconazole were melted together. The itraconazole went into solution at 140° C. To this molten mixture was added 1.25 grams of hydroxypropylmethylcellulose E4M which thickened the molten mixture to a greater extent and more rapidly than had been observed in Example 3. This dispersion was then granulated with a mixture of 12.5 grams of Avicel® PH-101 and 12.5 grams of croscarmellose sodium. Dissolution testing determined that 47% of the itraconazole had dissolved in 30 minutes. After 60 minutes this value had increased to 56%.

EXAMPLE 5

A stainless steel beaker containing 180 grams of glyceryl monostearate (Eastman Chemical Company) was heated to 100° C. When the glyceryl monostearate had melted, the temperature was increased to 145° C., and then 180 grams of crystalline itraconazole was added slowly while maintaining the temperature between 145° C. and 155° C. Stirring was continued until the itraconazole was fully dissolved, yielding a clear solution. To this solution was added 120 grams of hydroxypropylmethylcellulose E5 (Dow Chemical Company) with continued stirring. Simultaneously, a mixture of 60 grams of microcrystalline cellulose (Avicel® PH-101, FMC Corporation) and 60 grams of croscarmellose sodium (Ac-Di-Sol®, FMC Corporation) was placed in a high shear granulator bowl cooled to −4.2° C. The molten mixture was then added to the solids in the granulator bowl at a rate to maintain the temperature of the granulation below 5° C. The blade of the granulator was operated at 312 rpm with the chopper at #1 setting. Upon completion of the addition of the molten mixture, mixing was continued for an additional five minutes until the temperature was below −1° C. The granulation required 95 minutes to complete. This granulation was milled while being cooled with liquid nitrogen through a coarse screen. A second milling operation, also cooled with liquid nitrogen, was accomplished using a Fitz mill, Model M5 fitted with a 60 mesh (250 micron) wire screen. The finished granulation was suitable for use in filling hard gelatin capsules. These granules when tested for dissolution in simulated gastric juice at 37° C. were shown to provide solutions containing 86% of the available itraconazole after 30 minutes. This value increased to 95% after 60 minutes. After three hours under the conditions described above, 100% of the itraconazole had dissolved.

EXAMPLE 6

In a stirred kettle heated to 150–165° C. was placed on 0.25 Kg of glyceryl monostearate. When the glyceryl monostearate was completely molten, the slow addition of 1.5 Kg of itraconazole was begun. Upon completion of addition, the mixture was heated and stirred until all of the itraconazole was completely dissolved. Simultaneously, a dry blend of 2.25 Kg of hydroxypropylmethylcellulose E5 (Dow Chemical Company) and 0.60 Kg of croscarmellose sodium (Ac-Di-Sol®, FMC Corporation) was placed in a high shear granulator heated to 150° C. After the dry mixture had attained a temperature of 150° C. and, with the main blade of the granulator operating at 300 rpm and the cross screw operated at full speed, the molten mixture of glyceryl monostearate and itraconazole was pumped from the kettle into the granulator during a period of one minute. After 1.5 minutes of granulation, the granulated mixture was discharged into a stream of liquid nitrogen, rapidly cooling and solidifying the granulate. The granulate was milled using a Fitz mill, Model M5, fitted with a 1512-0027 perforated screen, and cooled with liquid nitrogen. The milled granulate was then placed in a twin shell blender, and 0.4 Kg of Avicel Ph-200 was added and blended to prepare the final formulation to be used to fill hard gelatin capsules. Using the test conditions described in Example 5, the powdered granulate provided dissolution of 87% after 30 minutes and 94% after one hour. For comparison, the capsules provided 84% dissolution after 30 minutes and 98% after one hour, indicating that there was no significant difference between the two dissolution tests.

EXAMPLE 7

In a separate run, the granular particles of this example were prepared, milled and blended as provided in example 6, except that the granular particle was blended with 0.25 Kg of microcrystalline cellulose and 0.15 Kg talc to facilitate blending and handling of the finished formulation. The finished blend of granular particles and additives thus contains 30% itraconazole, 5% glyceryl monostearate, 12% croscarmellose sodium, 45% HPMC, 5% microcrystalline cellulose and 3% talc, by weight of the resulting blend. The dissolution results were consistent with those obtained for example six.

We claim:
1. A granular particle comprsing:
   (a) a solid solution of an amorphous, pharmaceutically active agent and a pharmaceutically acceptable hydrophobic vehicle, wherein said pharmaceutically active agent is normally crystalline and sparingly-water soluble;
   (b) a stabilizer comprising a polyethylene glycol, sugars, sorbitol, mannitol, polyvinylpyrrolidone, or one or more cellulose ethers; and
   (c) a disintegrant comprising croscarmellose sodium, sodium starch glycolate, crospovidone, or a cross-linked polyacrylate.
2. The granular particle of claim 1, in which the pharmaceutically active agent is an azole fungicide.
3. The granular particle of claim 2, in which the azole fungicide is itraconazole.

4. The granular particle of claim 3, in which itraconazole is present at about 5% to about 60% by dry weight of the granular particle.

5. The granular particle of claim 4, in which itraconazole is present at about 20% to about 35% by dry weight of the granular particle.

6. The granular particle of claim 1, in which the hydrophobic vehicle comprises glyceryl monostearate, a monoglyceride, a diglyceride, a triglyceride, or a wax.

7. The granular particle of claim 6, in which the hydrophobic vehicle comprises glyceryl monostearate.

8. The granular particle of claim 7, in which the glyceryl monostearate is present in the range of about 3% to about 55% by dry weight of the granular particle.

9. The granular particle of claim 8, in which the glyceryl monostearate is present at about 5% to about 35% by dry weight of the granular particle.

10. The granular particle of claim 1, in which the stabilizer is hydroxypropylmethylcellulose.

11. The granular particle of claim 10, in which the hydroxypropylmethylcellulose is present at about 1% to about 60% by dry weight of the granular particle.

12. The granular particle of claim 1, in which the disintegrant is croscarmellose and is present at about 1% to about 25% by dry weight of the granular particle.

13. The granular particle of claim 1, further comprising a binder comprising microcrystalline cellulose, flocculated cellulose, starch, a sugar, calcium phosphate, calcium carbonate or kaolin.

14. The granular particle of claim 13, in which the binder is microcrystalline cellulose and is present at about 5% to about 35% by dry weight of the granular particle.

15. A granular particle comprising:
   (a) a stabilized solid solution of amorphous itraconazole and a pharmaceutically acceptable hydrophobic vehicle;
   (b) a stabilizer comprising a polyethylene glycol, sugars, sorbitol, mannitol, polyvinyl pyrrolidone, or one or more cellulose ethers; and
   (c) a disintegrant comprising croscarmellose sodium, sodium starch glycolate, crospovidone, or a cross-linked polyacrylate;
   wherein said granular particle is made by a process which comprises the steps of:
      (i) heating the hydrophobic vehicle to a temperature to form a molten hydrophobic vehicle and at which said itraconazole dissolves in the molten hydrophobic vehicle;
      (ii) dissolving said itraconazole in the molten hydrophobic vehicle to form a molten solution of itraconazole in hydrophobic vehicle; then
      (iii) adding a stabilizing amount of said stabilizer to said molten solution of itraconazole in hydrophobic vehicle; and
      (iv) granulating the molten mixture from step (iii) with a cooled disintegrant and optionally a binder, at a temperature below 30° C. to form the granular particle comprising the solid solution of itraconazole stabilized in amorphous form in said hydrophobic vehicle.

16. A granular particle comprising:
   (a) a stabilized solid solution of amorphous itraconazole and a pharmaceutically acceptable hydrophobic vehicle;
   (b) a stabilizer comprising a polyethylene glycol, sugars, sorbitol, mannitol, polyvinyl pyrrolidone, or one more cellulose ethers; and
   (c) a disintegrant comprising croscarmellose sodium, sodium starch glycolate, crospovidone, or a cross-linked polyacrylate;
   wherein said granular particle is made by a process which comprises the steps of:
      (i) heating the hydrophobic vehicle to a temperature to form a molten hydrophobic vehicle and at which said itraconazole dissolves in the molten hydrophobic vehicle;
      (ii) dissolving said itraconazole in the molten hydrophobic vehicle to form a molten solution of itraconazole in hydrophobic vehicle; then
      (iii) granulating molten solution of itraconazole in hydrophobic vehicle from step (ii) with the stabilizer, the disintegrant and optionally a binder, at a temperature of at least a temperature at which the itraconazole dissolves in the hydrophobic vehicle; and
      (iv) cooling the resulting granulation.

17. A granular particle comprising:
   (a) a solid solution of amorphous itraconazole and glycerol monostearate, wherein said itraconazole is normally crystalline, sparingly water-soluble, and present in an amount of about 20% to about 35% by dry weight of said granular particle, and said glycerol monostearate is present in an amount of about 5% to about 35% by dry weight of said granular particle;
   (b) a stabilizer comprising a hydroxypropylmethylcellulose in an amount of about 1% to about 50% by dry weight of said granular particle; and
   (c) a disintegrant comprising croscarmellose sodium in an amount of about 3% to about 25% by dry weight of said granular particle.

18. The granular particle of claim 17, comprising about 15% to about 25% hydroxypropylmethylcellulose by dry weight of said granular particle and further comprising about 5% to about 15% microcrystalline cellulose by dry weight of said granular particle.

19. The granular particle of claim 17, wherein said itraconazole is present in an amount of about 30% to about 35% by dry weight of said granular particle, said glycerol monostearate is present in an amount of 5% to 15% by dry weight of said granular particle, said croscarmellose sodium is present in an amount of about 10% to 15% by dry weight of said granular particle and said hydroxypropylmethylcellulose is present in an amount of 45% to about 55% by dry weight of said granular particle.

20. A granular particle comprising:
   (a) a stabilized solid solution of amorphous itraconazole and glycerol monostearate, wherein said itraconazole is present in an amount of about 20%, to about 35% by dry weight of said granular particle, and said glycerol monostearate is present in an amount of about 5% to about 35% by dry weight of said granular particle;
   (b) a stabilizer comprising hydroxypropylmethyl cellulose in an amount of about 1% to about 50% by dry weight of said granular particle; and
   (c) a disintegrant comprising croscarmellose sodium in an amount of about 3% to about 25% by dry weight of said granular particle;
   wherein said granular particle is made, by a process which comprises the steps of:
      (i) heating the glycerol monostearate to a temperature to form molten glycerol monostearate and at which said itraconazole dissolves in the molten glycerol monostearate;

(ii) dissolving said itraconazole in the molten glycerol monostearate to form a molten solution of itraconazole in glycerol monostearate; then (iii) adding a stabilizing amount of said hydroxypropylmethyl cellulose to said molten solution of itraconazole in glycerol monostearate; and (iv) granulating the molten mixture from step (iii) with a cooled croscarmellose, sodium and optionally a binder, at a temperature below 30° C. to form the granular particle comprising the solid solution of itraconazole stabilized in amorphous form in said glycerol monostearate.

21. A granular particle comprising:

(a) a stabilized solid solution of amorphous itraconazole and a glycerol monostearate, wherein said itraconazole is present in an amount of about 20% to about 35% by dry weight of said granular particle, and said glycerol monostearate is present in an amount of about 5% to about 35% by dry weight of said granular particle;

(b) a stabilizer comprising a hydroxypropylmethylcellulose in an amount of about 1% to about 50% by dry weight of said granular particle; and (c) a disintegrant comprising croscarmellose sodium in an amount of about 3% to about 25% by dry weight of said granular particle;

wherein said granular particle is made by a process which comprises the steps of:

(i) heating the glycerol monostearate to a temperature to form a molten glycerol monostearate and at which said itraconazole dissolves in the molten glycerol monostearate;

(ii) dissolving said itraconazole in the molten glycerol monostearate to form a molten solution of itraconazole in glycerol monostearate; then (iii) granulating molten solution of itraconazole in glycerol monostearate from step (ii) with the stabilizer, the disintegrant and optionally a binder, at a temperature of at least a temperature at which the itraconazole dissolves in the glycerol monostearate; and (iv) cooling the resulting granulation.

* * * * *